United States Patent [19]

Squyres et al.

[11] Patent Number: 5,419,438
[45] Date of Patent: May 30, 1995

[54] APPARATUS AND METHOD FOR SORTING POST-CONSUMER ARTICLES ACCORDING TO PVC CONTENT

[75] Inventors: H. Parks Squyres; William S. Drummond, both of Medford, Oreg.

[73] Assignee: Simco/Ramic Corporation, Medford, Oreg.

[21] Appl. No.: 157,839

[22] Filed: Nov. 24, 1993

[51] Int. Cl.⁶ .............................................. B07C 5/02
[52] U.S. Cl. .................................. 209/3.1; 209/578; 209/587; 250/461.1; 356/51
[58] Field of Search .................... 209/3, 3.1, 578, 587; 250/461.1, 458.1, 459.1; 356/51

[56] References Cited

U.S. PATENT DOCUMENTS

| | | | |
|---|---|---|---|
| 2,717,693 | 9/1955 | Holmes | 209/72 |
| 3,305,089 | 2/1967 | Fraenkel | 209/578 X |
| 4,347,125 | 8/1982 | Di Giacomo | 209/578 X |
| 4,360,539 | 11/1982 | Sachtleben et al. | 427/8 |
| 4,778,593 | 10/1988 | Yamashita et al. | 209/3.1 |
| 4,789,965 | 12/1988 | Michl et al. | |
| 4,866,283 | 9/1989 | Hill, Jr. | 209/578 X |
| 5,084,135 | 1/1992 | Brooks et al. | 209/3 X |
| 5,134,291 | 7/1992 | Ruhl, Jr. et al. | 250/341 |
| 5,141,110 | 8/1992 | Trischan et al. | 209/524 |
| 5,183,212 | 2/1993 | Boo et al. | 209/3 X |
| 5,201,921 | 4/1993 | Luttermann et al. | 8/506 |
| 5,234,110 | 8/1993 | Kobler | 209/3 X |
| 5,268,074 | 12/1993 | Brooks et al. | 209/3 X |
| 5,277,758 | 1/1994 | Brooks et al. | 209/3 X |
| 5,295,582 | 3/1994 | Dan | 209/3 |

FOREIGN PATENT DOCUMENTS

| | | |
|---|---|---|
| 0291959 | 11/1988 | European Pat. Off. |
| 2052736 | 1/1981 | United Kingdom ............... 269/578 |
| 2234347 | 1/1991 | United Kingdom . |

*Primary Examiner*—D. Glenn Dayoan
*Attorney, Agent, or Firm*—Stoel Rives Boley Jones & Grey

[57] ABSTRACT

In a preferred embodiment, a sorting apparatus according to the present invention includes a conveyor belt for carrying a stream randomly-arranged articles, at least some of which are post-consumer plastic articles made of PVC and others of which are made of PET. The conveyor belt carries the articles to an irradiation area where they are irradiated with ultraviolet light that induces the post-consumer articles of PVC to emit phosphorescent light that persists after the irradiation ends. The conveyor belt then carries the articles to an inspection zone that is isolated from the ultraviolet light. A video camera is positioned to receive phosphorescent light emitted from post-consumer articles made of PVC. Other articles commonly in the stream of post-consumer plastic articles (e.g., PET) do not emit phosphorescent light and are, therefore, distinguishable from the PVC articles.

20 Claims, 2 Drawing Sheets

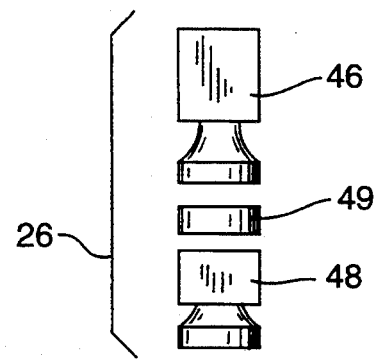
FIG. 2
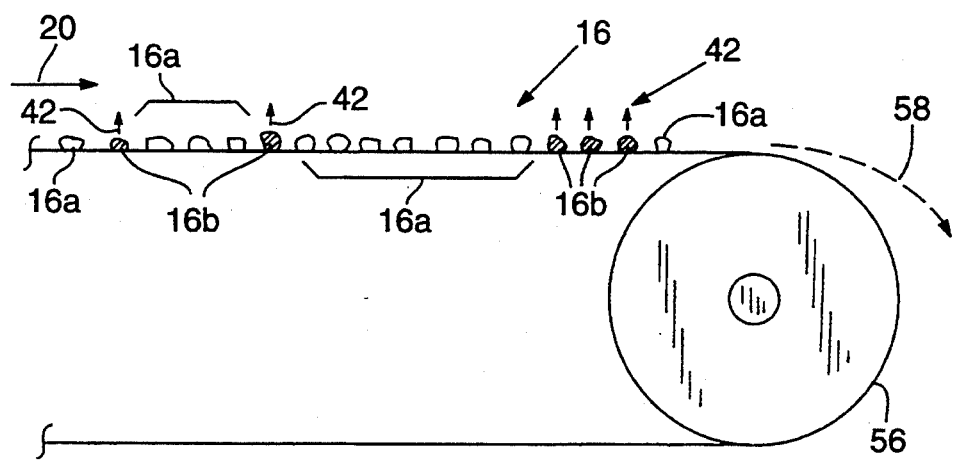
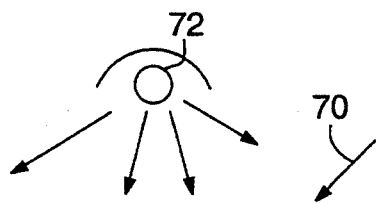
FIG. 3
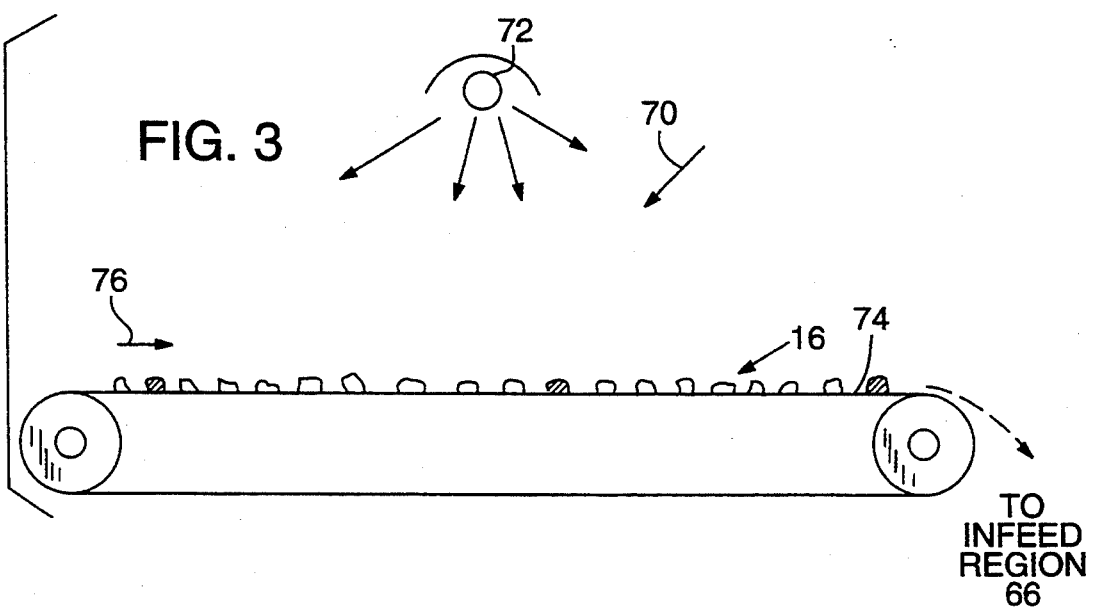

APPARATUS AND METHOD FOR SORTING POST-CONSUMER ARTICLES ACCORDING TO PVC CONTENT

TECHNICAL FIELD

This invention relates to sorting systems and, in particular, to an apparatus and a method for sorting post-consumer plastic articles including polyvinyl chloride from other articles.

BACKGROUND OF THE INVENTION

Growing environmental awareness has developed a market for recycled plastic articles. Recycling of plastic articles is desireable because they are made from nonrenewable petrochemical resources, consume diminishing landfill space, and decompose very slowly. The market for recycled plastic is cost-sensitive, and removing contaminants from different types of post-consumer plastics is a major cost of processing them. Accordingly, high-speed, automated sorting systems are needed to sort foreign materials, including different types of plastics, from post-consumer plastic articles.

Many post-consumer plastic articles are containers, such as beverage containers, that are of a single plastic, such as polyvinyl chloride (PVC) or polyethylene terephthalate (PET). The wide availability of PVC and PET as post-consumer materials make them relatively desireable for recycling.

Articles made of PVC and PET have many common characteristics, such as density, optical transmissivity, and color, and are therefore difficult to sort automatically. However, these two plastics are chemically distinct and PVC, in particular, is considered a contaminant of PET when intermixed during recycling. Such contaminants are difficult to remove during the recycling process and, therefore, greatly diminish the value of the recycled PET plastic.

Some post-consumer plastics sorting systems, such as that described in U.S. Pat. No. 5,141,110 of Trischan et al., seek to sort whole post-consumer containers made of PET and PVC. Such systems can suffer from relatively low throughputs and are incapable of removing from the recycled articles attached foreign objects, such as container caps or tops that remain attached by consumers. Moreover, recycling of post-consumer plastic articles typically includes shredding or flaking the items before subsequent processing. Conventional automated sorting systems can have difficulty distinguishing flakes of PVC from PET.

SUMMARY OF THE INVENTION

An object of the present invention is, therefore, to provide an apparatus and a method for sorting post-consumer plastic articles.

Another object of this invention is to provide such an apparatus and a method for sorting post-consumer PVC articles from post-consumer PET articles.

A further object of this invention is to separate flaked post-consumer PVC products from flaked post-consumer PET products.

Still another object of this invention is to provide such an apparatus and a method for sorting articles at a high throughput.

In a preferred embodiment, a sorting apparatus according to the present invention includes one or more conveyor belts for carrying a stream of randomly-arranged articles, at least some of which are pieces of post-consumer plastic products made of PVC and others of which are made of PET. A conveyor belt carries the articles to an irradiation area where they are irradiated with ultraviolet light that induces the post-consumer articles of PVC to emit phosphorescent light that persists after the irradiation ends.

A conveyor belt then carries the articles to an inspection zone that is isolated from both the ultraviolet light and most ambient light. A video camera is positioned to receive phosphorescent light emitted from post-consumer articles made of PVC. Other articles commonly in a stream of post-consumer plastic articles (e.g., PET) do not emit phosphorescent light and are, therefore, not detected by the video camera. The isolation of the inspection zone prevents the ultraviolet light from inducing fluorescence (i.e., light emission contemporaneous with irradiation) in various articles, such as PET. Such fluorescence could make it difficult to distinguish PVC from other fluorescent materials such as PET.

The video camera generates a video signal representative of the light it receives. A processor receives the video signal and processes it to identify the phosphorescent articles within the inspection zone (i.e., the articles that include PVC). In coordination with the movement of the conveyor belt and the location thereon of the articles that include PVC, the processor activates a separator to separate the PVC articles from the other ones. Accordingly, the sorting system of the present invention is capable of providing high throughput, accurate sorting of post-consumer PVC articles from post-consumer PET articles.

Additional objects and advantages of this invention will be apparent from the following detailed description of a preferred embodiment thereof which proceeds with reference to the accompanying drawings.

BRIEF DESCRIPTION OF THE DRAWINGS

FIG. 2 is a diagrammatic side view showing the inspection zone of the sorting system of FIG. 1.

FIG. 3 is a diagrammatic side view of an alternative ultraviolet irradiation system.

DETAILED DESCRIPTION OF PREFERRED EMBODIMENT

Figure 1:
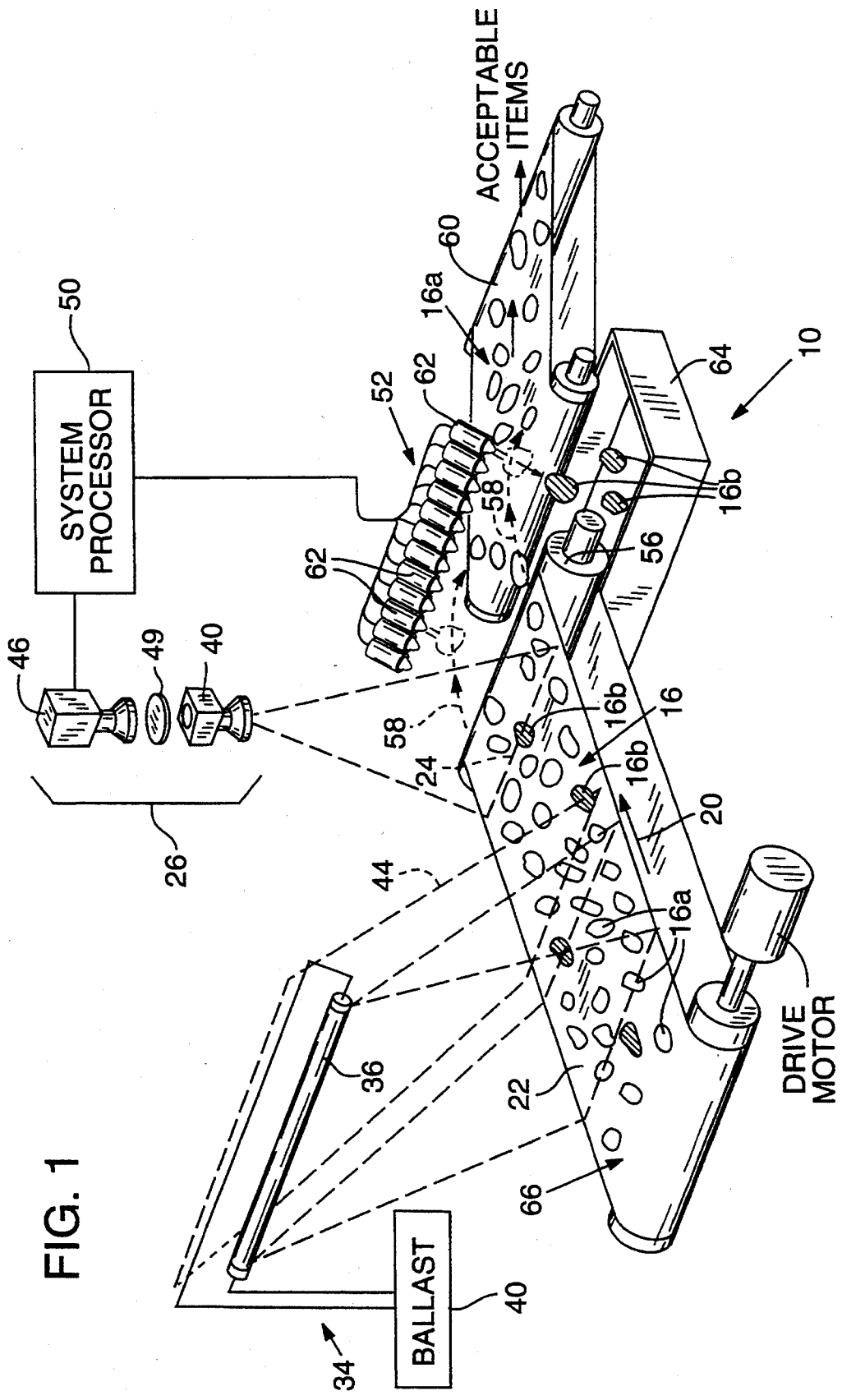
FIG. 1 is a combined diagrammatic side elevation and block diagram of a sorting system of the present invention.

Referring to FIGS. 1 and 2, a sorting system 10 of the present invention sorts articles 16 randomly scattered on a conveyor belt 18 that moves in a direction 20 successively through an irradiation zone 22 and an inspection zone 24. Belt 18 carries multiple articles 16 at a time through irradiating zone 22 and inspection zone 24, the latter of which is defined by a field of view of an image detector 26.

Most of articles 16 include polyethylene terephthalate (PET) and are referred to herein as PET articles 16a. Other articles 16 include polyvinyl chloride (PVC), are referred to as PVC articles 16b, and are designated by hatching. In the preferred embodiment, PET articles 16a and PVC articles 16B are pieces of post-consumer plastic products, such as food and beverage containers, and PVC articles 16b are considered an undesirable contaminant of PET articles 16a. It will be appreciated, however, that sorting system 10 could be operated according to other sorting objectives.

An ultraviolet light source 34 is positioned in irradiation zone 22 over conveyor belt 18 to irradiate articles 16 with ultraviolet light 36 of a wavelength that induces phosphorescence in PVC articles 16b. Suitable light includes short wave ultraviolet light, particularly with wavelengths between 235 nm and 255 nm generated, for example, by a c.w. ion laser at 238 nm and 248 nm or a quartz lamp at 253.7 nm. Light source 34 preferably includes a lamp 36 of the quartz low pressure mercury U.V. type, such as Model No. G64T5VH from Light Sources Inc. of Milford, Conn., driven by a ballast 40, such as a Model I564PUV from Robertsons Inc. of Blue Island, Ill. For example, lamp 36 can be driven with 65 watts of input power to generate 25 watts of output power at 253.7 nm.

Image detector 26 is positioned to receive phosphorescent light 42 emitted from PVC articles 16b in response to irradiation by light source 34. Light 42 is considered phosphorescent in that its emission persists after irradiation by light source 34 ends. Phosphorescent light 42 from PVC articles 16b has been observed in the blue-green range of the electromagnetic spectrum at frequencies of 400–500 nm. The phosphorescent effect in PVC articles 16b appears to undergo exponential decay with a time constant on the order of a few tenths of a second. As a result, phosphorescent light 42 from PVC articles 16b is substantially undetectable 10–20 seconds after irradiation.

A light baffle or isolation panel 44 is positioned between irradiation zone 22 and inspection zone 24 to prevent light from light source 34 from reaching inspection zone 24. Isolation panel 44 prevents ultraviolet light 36 from reaching in inspection zone 24 PET articles 16a that emit fluorescent light (i.e., light emission that is contemporaneous with irradiation) while under such irradiation.

It will be appreciated, however, that isolation between irradiation zone 22 and inspection zone 24 can be achieved in other ways. For example, zones 22 and 24 could be a common location at which irradiation and inspection is performed time-sequentially. Isolation could also be achieved by providing sufficient distance between zones 22 and 24 or a non-linear conveyor that moves articles 16 around a panel 44.

In one embodiment, isolation panel 44 prevents ambient light from reaching inspection zone 24, as well as ultraviolet light from light source 34. In another embodiment, certain ambient light may be allowed into inspection zone 24. More specifically, sorting system 10 may be operated in red ambient light to simplify isolation panel 44 while providing light for operators to see sorting system 10. Red light is desirable because it is distinct from the blue-green light emitted from PVC articles 16b and a red-cut light filter on image detector 26 can prevent the red light from reaching video camera 46.

In response to the ultraviolet irradiation provided by light source 34, PVC articles 16b emit phosphorescent light in inspection zone 24, but PET articles 16a emit no light. As a result, image detector 26 can distinguish PVC articles 16b from PET articles 16a. Image detector 26 includes a video camera 46, an image intensifier 48, and a fiber-optic coupler 49 positioned therebetween. Image intensifier 48 and fiber-optic coupler 46 provide video camera 46 with a brightness-enhanced image of articles 16 in inspection zone 24. Image intensifier 48, such as Model No. XX1560 from B.V. Delft Electonische Producten of Roden, Netherlands, is capable of enhancing the brightness of PVC articles 16b by factors as high as 100,000 so that video camera 46 can operate at high scan rates (e.g., 1.0 millisecond) compatible with high speed operation of sorting system 10.

Video camera 46 generates a video signal representing the light it receives. A system processor 50 receives the video signal and processes it to identify PVC articles 16b. In coordination with the movement of conveyor belt 18, processor 50 activates a separator 52 to separate PVC articles 16b from PET articles 16a. Preferably, conveyor belt 18 carries all articles 16 past inspection zone 24 to an outfeed bar or roller 56 from which articles 16 are projected along a trajectory 58 toward an acceptance conveyor belt 60. Whenever processor 50 determines that an article 16 is a PVC article 16b, processor 50 generates an activation signal to activate at least one of multiple fluid ejector modules 62 in separator 52. In response to the activation signal, an ejector module 62 releases a blast of air that deflects the PVC article 16b from trajectory 58 toward a reject chute 64. The remaining PET articles 16a pass to acceptance conveyor belt 60 for further processing.

Video camera 46 is preferably of the monochrome CCD array line-scan type with a lens and aperture suitable for the application and desired resolution, and processor 50 processes the video signal with digital circuitry. U.S. Pat. No. 5,085,325 of Jones et al., assigned to the assignee of the present invention and hereby incorporated by reference, describes a color sorting system that could be simplified for operation with a monochrome video camera for use in sorting system 10.

It will be appreciated by persons skilled in the art, however, that many other implementations are available for video camera 46, processor 50, and separator 52. For example, video camera 46 could detect color (e.g., Red-Green-Blue) characteristics of articles 16, and processor 50 could process the video signal with analog circuitry. Alternatively, sorting system 10 could employ photodetectors other than video camera 46 such as, for example, a photomultiplier tube or avalanche photodiodes.

Sorting system 10 preferably receives and sorts articles 16 that include pieces of post-consumer plastic products (e.g., PVC and PET products). The post-consumer plastic products are preferably formed into pieces or flakes by a granulator, as is known in the art, and cleaned before being delivered to conveyor belt 18 at an infeed region 66.

In an alternative method of operating sorting system 10, articles 16 are subjected to prolonged (e.g., 30 seconds) irradiation with ultraviolet light before being delivered to infeed region of conveyor belt 18. For example, such prior irradiation could be performed while post-consumer products are fed into a granulator or while carried therefrom to infeed region 66.

FIG. 3 shows an alternative ultraviolet irradiation system 70 having an ultraviolet light 72 that irradiates articles 16 while they are carried on a belt 74 in a direction 76 toward infeed region 66. Prior ultraviolet irradiation of this type has been found to allow brief subsequent irradiation to re-excite high-level phosphorescence from PVC, thereby facilitating high speed operation of sorting system 10.

For example, an initial ultraviolet irradiation of articles 16 for a period of 30 seconds could result in a high level of peak phosphorescence among PVC articles 16b. Over a subsequent period of about 30 seconds without ultraviolet irradiation, the phosphorescence resulting from the initial irradiation would decay to levels below detectability. A subsequent ultraviolet irradiation for a period of about one second, such as by light source 34, causes PVC articles 16b to phosphoresce at about 60% of the peak phosphorescence achieved by the prior irradiation. As a result, prolonged initial irradiation of articles 16 at a relatively slow-moving recycling stage, followed by brief subsequent irradiation can allow sorting system 10 to operate at a high speed with a light source 34 of reasonable size and power requirements.

In another alternative method of operating sorting system 10, articles 16 are cleaned in an alkali solution, preferably at a temperature greater than 200° F. (93° C.), before being delivered to infeed region 66 of conveyor belt 18. Such cleaning is a common step in the processing of post-consumer plastic articles. In connection with the operation of sorting system 10, however, such cleaning has been found to enhance phosphorescence of PVC articles 16b by factors of 2-50, thereby improving the detectability of PVC articles 16b. Such enhanced phosphorescence can also be obtained by cleaning articles 16 in tap water. It will be appreciated that these alternative methods of operating sorting system 10 could be employed separately or together.

It will be obvious to those having skill in the art that many changes may be made to the details of the above-described embodiment of this invention without departing from the underlying principles thereof. The scope of the present invention should be determined, therefore, only by the following claims.

We claim:

1. A method of sorting plural post-consumer articles according to the presence of polyvinyl chloride in the articles, comprising the steps of:
    irradiating the post-consumer articles with ultraviolet light for an irradiation period;
    isolating the post-consumer articles from the ultraviolet light and then detecting phosphorescent light emitted from the post-consumer articles in response to having been irradiated during the irradiation period; and
    sorting the post-consumer articles according to whether phosphorescent light is emitted therefrom, whereby the post-consumer articles including polyvinyl chloride emit phosphorescent light.

2. The method of claim 1 in which the plural post-consumer articles include articles having polyethylene terephthalate.

3. The method of claim 1 in which the ultraviolet light has a wavelength of between 235 nm and 255 nm.

4. The method of claim 1 further comprising the step of passing the post-consumer articles through a wash solution before the step of irradiating them.

5. The method of claim 4 in which the wash solution is alkaline.

6. The method of claim 5 in which the alkali wash solution is at a temperature greater than 93° C.

7. The method of claim 4 in which the wash solution is water.

8. The method of claim 1 further comprising the step of forming the post-consumer articles by reducing into pieces whole post-consumer products before the step of irradiating the post-consumer articles.

9. The method of claim 1 in which the step of detecting of phosphorescent light includes forming a brightness intensified image of the phosphorescent light emitted from the post-consumer articles.

10. A method of sorting plural post-consumer articles according to the presence of polyvinyl chloride in the articles, comprising the steps of:
    irradiating the post-consumer articles with ultraviolet light for separate first and second irradiation periods;
    after the first and second irradiation periods, detecting phosphorescent light emitted from the post-consumer articles in response to having been irradiated during the first and second irradiation periods; and
    sorting the post-consumer articles according to whether phosphorescent light is emitted therefrom, whereby the post-consumer articles including polyvinyl chloride emit phosphorescent light.

11. The method of claim 10 in which the second irradiation period follows and is of a duration less than that of the first irradiation period.

12. A post-consumer plastics sorting system that sorts post-consumer plastic articles including polyvinyl chloride from those without, comprising:
    an ultraviolet light source positioned to irradiate the post-consumer plastic articles with ultraviolet light;
    a conveyor for carrying plural post-consumer plastic articles irradiated by the ultraviolet light source to an inspection area;
    isolation means for preventing ultraviolet light from the ultraviolet light source from reaching the post-consumer plastic articles in the inspection area;
    a light detector in optical communication with the inspection area to detect therefrom phosphorescent light emitted from the post-consumer plastic articles including polyvinyl chloride in response to having been irradiated by the ultraviolet light source, the light detector generating a light signal corresponding to detected phosphorescent light;
    a processor receiving and processing the light signal from the light detector to identify the post-consumer plastic articles including polyvinyl chloride;
    a separator responsive to the processor for separating the post-consumer plastic articles including polyvinyl chloride from those without.

13. The system of claim 12 in which the post-consumer plastic articles without polyvinyl chloride primarily comprise polyethylene terephthalate.

14. The system of claim 12 in which the ultraviolet light source generates ultraviolet light with a wavelength of between 235 nm and 255 nm.

15. The system of claim 12 in which the light detector includes a light intensifier that intensifies phosphorescent light emitted from the post-consumer plastic articles and a video camera in communication with the light intensifier for generating the light signal.

16. The system of claim 12 further comprising a preliminary ultraviolet light source for irradiating the post-consumer plastic articles prior to their placement on the conveyor.

17. The system of claim 12 in which the light detector includes a light filter for blocking red light and the system is operated in red ambient light.

18. The system of claim 12 in which the light detector includes a video camera for generating the light signal and an image intensifier for providing to the video camera a brightness intensified image of the phosphorescent light emitted from the post-consumer articles.

19. A method of sorting plural post-consumer articles according to the presence of polyvinyl chloride in the articles, comprising the steps of:

irradiating the post-consumer articles with ultraviolet light for an irradiation period;

after the irradiation period, detecting phosphorescent light emitted from the post-consumer articles in response to having been irradiated during the irradiation period, the detecting step including forming a brightness intensified image of the phosphorescent light and generating from the brightness intensified image a light signal corresponding to the phosphorescent light.

20. The method of claim 19 further comprising the step of isolating the post-consumer articles from the ultraviolet light prior to detecting the phosphorescent light.

* * * * *